United States Patent [19]

Biener

[11] Patent Number: 4,943,432

[45] Date of Patent: Jul. 24, 1990

[54] SALT MIXTURE FOR THE TREATMENT OF PSORIASIS

[76] Inventor: Hans F. Biener, Heilman Strasse 21, 8000 Munich 71, Fed. Rep. of Germany

[21] Appl. No.: 236,513

[22] Filed: Aug. 24, 1988

Related U.S. Application Data

[63] Continuation of Ser. No. 916,279, Oct. 7, 1986, abandoned.

[30] Foreign Application Priority Data

Oct. 8, 1985 [EP] European Pat. Off. ........ 85112766.2

[51] Int. Cl.$^5$ .............................................. A61K 33/30
[52] U.S. Cl. .................... 424/647; 514/863; 424/648
[58] Field of Search ......................... 424/145; 514/863

[56] References Cited

U.S. PATENT DOCUMENTS 3,856,941 12/1974 Turner ................................ 424/145

FOREIGN PATENT DOCUMENTS 1192493 8/1985 Canada ................................ 424/153
8404885 12/1984 World Int. Prop. O. .

OTHER PUBLICATIONS

Azizi et al–Israel Journal of Medical Sciences, vol. 18, 1972, pp. 267–270.
Shani et al–Pharmacological Research Communications, vol. 17, No. 6, 1985, pp. 501–512.
Spiegler–"Salt Water Purification", 1962, John Wiley & Sons, Inc., p. 11.
Leiste–Abstract #786497-B, Curative Bath Concentrates-, DT-2124735, 11-1972.

*Primary Examiner*—Leonard Schenkman
*Attorney, Agent, or Firm*—Perman & Green

[57] ABSTRACT

A composition for the treatment of psoriasis and other skin diseases comprising a salt mixture of defined purity, which is applied to the diseased skin in solution or in gelled form. The composition may be characterized as composed primarily of a mixture of a magnesium halide, such as magnesium chloride, with mixed alkali and alkaline earth metal salts such as sodium and potassium chloride and/or bromide and calcium chloride or bromide. Other cations present in the mixture include strontium, aluminum, iron, lithium and zinc, and the anions include sulphate, hydrogen carbonate, borate, fluoride, silicate, iodide and carbonate.

16 Claims, No Drawings

SALT MIXTURE FOR THE TREATMENT OF PSORIASIS

This is a continuation of co-pending application Ser. No. 916,279 filed on Oct. 7, 1986 now abandoned.

BACKGROUND OF THE INVENTION

Between 2% and 3% of the populations of Europe and of the United States suffers from Psoriasis Vulgaris. Since a genetic defect is involved, no therapeutic method can assure a long term cure. All courses of treatment aim, therefore, at freedom from symptoms for the longest possible time, as a rule 6–12 months.

Psoriasis, which according to experience, always recurs and which in particularly serious cases can even be life threatening, generally requires treating patients intermittently during their entire lifetime. The appearance of the disease in youth thus necessitates treatment spanning decades. Treatment risk increases with treatment length, since common substances such as corticosteroids evidence cumulative long term side effects. This corresponds to years of ultraviolet radiation in cases of dermatosis and melanoma, the so-called light-induced cancer.

The search for a natural risk-free treatment has, therefore, intensified in recent years. The most well known example is the Dead Sea bath treatment, which was known in antiquity. Dead Sea water contains about 26% by weight of mixed salts and solids. It is known from various studies, for example, E. Azizi et al, Israeli Journal of Medical Sciences, 18, p. 267 (1982) that in the treatment of psoriasis and other skin diseases an average of about 65% of patients given immersion treatments in Dead Sea water are rendered free of symptoms. In addition, 20% show an improvement such that in about 85% of the cases a positive effect is evident. Tests performed under my direction using solutions prepared by reconstituting salt mixtures obtained from Dead Sea salt deposits have exhibited approximately the same results.

This treatment has three critical disadvantages. First, the high cost of travel makes it possible only for a few. Second, older patients, especially, suffer from the hot, unaccustomed climate and the strains of the trip. Third, allergies and reactions attributed to the presence of impurities such as organic compounds, bitumens and oil tars, sewage residues and organic decomposition products are commonplace. It is well known that the Dead Sea has no drainage and has served for millenia as an irreversible repository for wastes, including in recent years hotel and industrial waste and last but not least the scale of thousands of Psoriasis sufferers. Since 1978 the Dead Sea has been considered chemically unbalanced. The lack of suitable microorganisms in the highly concentrated salt solution prevents waste materials from biodegrading.

The shipment of Dead Sea waters, including waters evaporated to dryness, is not practical on the basis of costs and due to energy requirements and corrosion problems. Nor would this method solve the problems of pollution, allergic and other reactions. The same applies to salts which could be obtained from salt formations, evaporation residues, and naturally occurring deposits in the Dead Sea. These are differentiated from the object of this patent application, among other ways, in that we are dealing with natural products with variable composition and above all variable purity, which contain or at any time could contain undefined materials or unknown materials.

It is also known that a certain percentage of patients must limit or interrupt the Dead Sea treatment, since in addition to allergies, other complaints such as circulatory problems arise, or the illness itself becomes worse.

The task of the present invention would thus be to find a solution which has comparable effectiveness without these disadvantages.

SUMMARY OF THE INVENTION

Applicant has now discovered a composition of matter which has shown to be a more effective treatment for psoriasis and other skin diseases when applied to and contacted with the skin while avoiding the disadvantages and complications attendant to known natural treatments such as described above. The composition comprises a synthetic mixture of salts ionically composed primarily of magnesium and alkali and alkaline earth metal cations and halogen anions. More specifically, the preferred salt mixture according to the present invention exhibits the following composition in grams/kilogram in the ionic state, with the remainder up to 1000 grams being water of hydration.

| Cations (g./kg salt mixture) | | Anions (g. /kg salt mixture) | |
|---|---|---|---|
| magnesium | 20 to 285 | chloride | 20 to 750 |
| sodium | 11 to 266 | bromide | 0.2 to 29 |
| calcium | 2 to 235 | sulfate | 0.2 to 22 |
| potassium | 2 to 95 | borate | 0.05 to 14 |
| strontium | 0.02 to 10.5 | silicate | 0.02 to 14 |
| iron | 0.02 to 8.5 | fluoride | 0.001 to 11 |
| aluminum | 0.001 to 6.0 | iodide | 0.001 to 9.5 |
| zinc | 0.001 to 2.5 | carbonate | 0.0002 to 9.0 |
| lithium | 0.001 to 2.0 | hydrogen carbonate | 0.0001 to 8.5 |

The composition may be applied to the affected area of the skin as an aqueous solution, or employed as a bath additive, or as a gel or salve.

DETAILED DESCRIPTION OF THE INVENTION

The salt mixture of the present invention contains many of the salts which are naturally present as components of Dead Sea water, but as pointed out above, does not contain essentially any of the impurities referred to above which are found in said waters and which detract from the therapeutic effect. Thus, the composition may be characterized as essentially free of organic impurities which for the purposes hereof are bitumens and oil tars, sewage residues and organic decomposition products, and is of defined purity. The composition may be characterized as composed primarily of a mixture of water soluble salts including a magnesium halide, such as magnesium chloride, with mixed alkali and alkaline earth metal salts such as sodium and potassium chloride and/or bromide and calcium chloride or bromide. Preferably at least about 99% by weight of the content of the salt mixture (not considering water of hydration) is composed of mixtures of these anions and cations. Other cations which are preferably present in the mixture include strontium, aluminium, iron, lithium and zinc, and the other anions include sulphate, hydrogen carbonate, borate, fluoride, silicate, iodide and carbonate. The most preferred composition of the mixture in grams/kilogram, with the remainder up to 1000 grams being water of hydration, is as follows:

| Cations (g./kg salt mixture) | | Anions (g./kg salt mixture) | |
|---|---|---|---|
| magnesium | 55 to 108 | chloride | 340 to 550 |
| sodium | 51 to 126 | bromide | 1.5 to 15 |
| calcium | 19 to 36 | sulfate | 1.1 to 9 |
| potassium | 10 to 21 | borate | 0.4 to 3 |
| strontium | 0.2 to 2.0 | silicate | 0.1 to 2.9 |
| iron | 0.18 to 1.9 | fluoride | 0.1 to 2.2 |
| aluminum | 0.006 to 1.2 | iodide | 0.1 to 2.0 |
| zinc | 0.02 to 0.8 | carbonate | 0.01 to 1.0 |
| lithium | 0.004 to 0.7 | hydrogen carbonate | 0.01 to 1.0 |

Bathing in solutions of salt mixtures prepared according to the invention, or respectively, the application of these mixtures to the skin, led to unexpectedly notable therapeutic effects. Especially surprising, however, is that even in hundreds of previously treated patients, not a single instance of allergic or similar reaction occurred, and that no treatment had to be terminated for the reasons cited in relation to the Dead Sea treatments. This very favorable finding was by no means to be expected and represents a substantial improvement in the method of treatment.

The invention's salt mixture was clinically tested in Germany and was approved by the German Federal Health Administration (BGA) as a prescription pharmaceutical on Oct. 26, 1984.

The invention's salt mixture has had correspondingly positive effects with acne, which appears so strongly in approximately 15% of European adolescents between the ages of 12-25 that treatment is warranted, for example in neurodermatitis, ichthyosis, and other skin diseases, including Hycosis fungiodes I-II, and Vitiligo.

In support of this treatment, which balneologically perhaps also derives from an increase of the serum bromine content, the invention can also be used in conjunction with exposure to ultraviolet light, sound, or electromagnetic radiation of desired wavelengths. Other known substances for skin treatment can also be utilized to advantage in support of the therapy, substances such as tar and tar derivatives, salicylic acid and derivatives and emollient and skin protective preparations, antiseptics, antimycotics, dermatics and/or light absorbent substances. These additives can also be worked into the salt mixture directly.

Similarly, it is also advantageous to vary the concentration of the invention's salt solutions, as well as bath temperature (for example, room temperature to about 50° C.) and duration, according to the patient's skin type. The concentration may generally range from about 0.1 up to about 34% by weight, more preferably from about 0.1 to about 26% by weight.

For example, one would undertake an initial salt concentration in a carrier medium, for example a water, gel or salve medium, of about 0.1 to 8% by weight in patients with strong skin lesions, preferably from about 0.5 to 8% by weight, while in other cases it is appropriate to speed the effect via concentrations of about 0.5 to approximately 34% by weight, more preferably from about 0.5 to 26% by weight most preferably from about 7 to about 26% by weight.

For lighter dosages the invention's salt mixture can also be used in granular or tablet form (if necessary with disintegrants) or also in a concentrated solution which is thinned prior to use. It has also been shown to be advantageous for patients who have undergone an initial bathing treatment such as described hereinbelow to bathe once or twice weekly in a very dilute water solution of the salt mixture of this invention, for example at a concentration of about 0.25% by weight, to prevent or retard a recurrence of the psoriasis symptoms.

A particularly advantageous use consists of applying the salt solution in gel instead of fluid form. This requires much less of the substance than bathing, and one can isolate certain parts of the body for and from treatment. The same holds for the application of compresses.

To produce the salt gel, the salt solution is gelled by means of mixing it with natural or synthetic gums or colloid additives as known in the art such as organic polymers, as described in the German patents DE 31 03 499 Al or 34 32 573 Al. Another especially preferred possibility is the use of cellulose esters or ethers, of which just 1%-2% by weight suffices. The gel can thus remain transparent, which offers advantages in additional ultraviolet exposure, or can be dyed, for example black for the absorption of infrared radiation. The same principle applies to the salt mixture.

The addition of 1%-20% glycol and especially of glycerin has proved very beneficial to stability and skin tolerance.

Other than in gel form, the invention's salt mixture can also be dispersed or emulsified as a solution or, for example, used in the customary salve bases.

The following Example and therapeutic data is illustrative of the invention:

EXAMPLE

A therapeutic composition was prepared by dry mixing the following ingredients (pharmaceutical grade):

| | | |
|---|---|---|
| 659 | grams | Magnesium chloride (MgCl$_2$.6H$_2$O) |
| 213 | " | Sodium chloride (NaCl) |
| 198 | " | Calcium chloride (CaCl$_2$.2H$_2$O) |
| 27 | " | Potassium chloride (KCl) |
| 12 | " | Sodium bromide (NaBr) |
| 5.4 | " | Magnesium sulphate (MgSO$_4$) |
| 1.5 | " | Strontium chloride (SrCl$_2$.6H$_2$O) |
| 0.4 | " | Sodium hydrogencarbonate (NaHCO$_3$) |
| 0.244 | " | Aluminum sulfate (Al$_2$SO$_4$.18H$_2$O) |
| 0.227 | " | Sodiumtetraborate (Na$_2$B$_4$O$_7$.10H$_2$O) |
| 0.190 | " | Lithium chloride (LiCl) |
| 0.105 | " | Iron sulphate (FeSO$_4$) |
| 0.094 | " | Sodium fluoride (NaF) |
| 0.087 | " | Sodium metasilicate (Na$_2$SiO$_3$) |
| 0.042 | " | Potassium iodide (KI) |
| 0.040 | " | Sodium carbonate (Na$_2$CO$_3$) |
| 0.018 | " | Zinc chloride (ZnCl$_2$) |

Patients suffering from psoriasis were treated by bathing twice daily for periods of twenty minutes each in a 12% by weight aqueous solution of the therapeutic composition of the Example at a bath temperature of about 35° C. to 36° C. The treatment was conducted by a dermatologist and assisting physician in a large treatment tub 12 meters long, 7 meters wide and 1.4 meters deep. This brine tub has a special reclining surface on which the psoriasis patient lies in approximately 20 centimeters of the brine water. The patients were also subjected to exposure to radiation from an ultraviolet lamp simultaneously with the bath treatment.

These treatments were repeated daily during a four to six week period.

After testing and evaluation of nearly 2,000 psoriasis sufferers subjected to the aforementioned treatment, it was observed that about 94% of them were rendered free of symptoms or at least exhibited an improvement of the condition, and in all cases without any allergic reactions. The treatment also proved to be effective in patients with up to 98% psoriatric skin change, which was never observed in analogous treatments using natural Dead Sea salts as the therapeutic agent.

These results are significantly better than those results observed where the therapeutic agent used was a 12% aqueous solution of evaporation residue of Dead Sea water. By comparison, patients previously treated in the same manner as set forth above with Dead Sea water residue showed only an 85% response to freedom from symptoms or improvement after the four to six week period. In addition, it was observed that there were fewer side effects, such as redness of skin, and no allergic reactions involved with the nearly 2,000 patients subjected to the treatment of this invention as compared with treatment using the natural Dead Sea salt as a consequence of which a significant minority of patients suffered from allergic reactions.

Clinical studies were also conducted wherein the composition of this invention in the form of a gel was applied to localized areas of the skin of psoriasis patients. The gel was prepared by dissolving the composition of the Example in water at an 8% by weight solids concentration. Two percent by weight of cellulose ester colloid (Natrosol® marketed by Hercules Corporation) was thoroughly mixed with the solution along with about 0.05% by weight of a preservative and it was allowed to gel.

The gel was applied daily to localized affected skin areas of psoriasis sufferers followed by exposure to ultraviolet radiation for about 20 minutes. Although the clinical tests have not yet been completed, it has been noted that positive responses have been observed in the majority of patients.

What I claim is:

1. A composition for the treatment of psoriasis by application to the skin, said composition prepared by forming a mixture of salt components such that the salt components are present in the mixture in the following proportions, expressed as grams/kilogram of salt mixture in the ionic state:

| Cations (g./kg salt mixture) | | Anions (g./kg salt mixture) | |
|---|---|---|---|
| magnesium | 55 to 108 | chloride | 340 to 550 |
| sodium | 51 to 126 | bromide | 1.5 to 15 |
| calcium | 19 to 36 | sulfate | 1.1 to 9 |
| potassium | 10 to 21 | borate | 0.4 to 3 |
| strontium | 0.2 to 2.0 | silicate | 0.1 to 2.9 |
| iron | 0.18 to 1.9 | fluoride | 0.1 to 2.2 |
| aluminum | 0.006 to 1.2 | iodide | 0.1 to 2.0 |
| zinc | 0.02 to 0.8 | carbonate | 0.01 to 1.0 |
| lithium | 0.004 to 0.7 | hydrogen carbonate | 0.01 to 1.0 | said composition further characterized as being essentially free of organic impurities.

2. A solution for the treatment of psoriasis by application to the skin, said solution prepared by dissolving the composition of claim 1 in water, said solution further characterized as being essentially free of organic impurities and having a solids concentration within the range of about 0.1 to about 34% by weight.

3. The solution of claim 2 wherein the solids concentration is within the range of about 0.5 to about 26% by weight.

4. The solution of claim 2 wherein the solids concentration of the solution is within the range of about 0.1 to about 26% by weight.

5. The solution of claim 4 wherein the solids concentration is within the range of about 7 to about 26% by weight.

6. A gel comprising the solution of claim 2 mixed with a sufficient amount of a natural or synthetic gum or colloid additive.

7. The gel of claim 6 wherein said additive is a cellulose ether or ester present at a level of about 1 to 2% by weight.

8. A composition for the treatment of psoriasis by application to the skin, said composition prepared by forming a mixture comprising the following components in the following approximate proportions:

| 659 | parts by wt. | Magnesium chlorid ($MgCl_2.6H_2O$) |
|---|---|---|
| 213 | " | Sodium chloride (NaCl) |
| 198 | " | Calcium chloride ($CaCl_2.2H_2O$) |
| 27 | " | Potassium chloride (KCl) |
| 12 | " | Sodium bromide (NaBr) |
| 5.4 | " | Magnesium sulphate ($MgSO_4$) |
| 1.5 | " | Strontium chloride ($SrCl_2.6H_2O$) |
| 0.4 | " | Sodium hydrogencarbonate ($NaHCO_3$) |
| 0.244 | " | Aluminum sulfate ($Al_2SO_4.18H_2O$) |
| 0.227 | " | Sodium tetraborate ($Na_2B_4O_7.10H_2O$) |
| 0.190 | " | Lithium chloride (LiCl) |
| 0.105 | " | Iron sulfate ($FeSO_4$) |
| 0.094 | " | Sodium fluoride (NaF) |
| 0.087 | " | Sodium metasilicate ($Na_2SiO_3$) |
| 0.042 | " | Potassium iodide (KI) |
| 0.040 | " | Sodium carbonate ($Na_2CO_3$) |
| 0.018 | " | Zinc chloride ($ZnCl_2$), | said composition further characterized as being essentially free of organic impurities.

9. A solution for the treatment of psoriasis by application to the skin, said solution prepared by dissolving the composition of claim 8 in water, said solution further characterized as being essentially free of organic impurities and having a solids concentration within the range of about 0.1 to about 34% by weight.

10. A method for treating psoriasis comprising contacting the affected skin areas with the solution of claim 9.

11. A method for treating psoriasis comprising contacting the affected skin areas with an aqueous solution of the composition of claim 1.

12. The method of claim 11 wherein the solid content of said solution is within the range of from about 0.5 to about 26% by weight.

13. The method of claim 12 wherein the affected skin areas are simultaneously exposed to ultraviolet radiation during at least a portion of said period of contact.

14. A method for treating psoriasis comprising contacting the affected skin areas with the solution of claim 4.

15. The method of claim 14 wherein the affected skin areas are simultaneously exposed to ultraviolet radiation during at least a portion of said period of contact.

16. A method for treating psoriasis comprising contacting the affected skin areas with the gel of claim 6.

* * * * *